United States Patent [19]
Gereg

[11] 4,449,693
[45] May 22, 1984

[54] CATHETER CHECK VALVE

[76] Inventor: Gordon A. Gereg, 159 Sawpit Hill Rd., Woodbury, Conn. 06798

[21] Appl. No.: 428,886

[22] Filed: Sep. 30, 1982

[51] Int. Cl.³ .............................................. F16L 37/28
[52] U.S. Cl. ..................... 251/149.8; 251/149; 604/236; 604/237; 604/283; 604/905
[58] Field of Search ............... 604/236, 237, 238, 256, 604/34, 905, 283; 251/149, 149.1, 149.7, 149.8, 4, 5

[56] References Cited

U.S. PATENT DOCUMENTS

| Re. 25,788 | 6/1965 | Sheridon | 604/283 |
| 605,693 | 6/1898 | Black | 137/843 |
| 3,601,151 | 8/1971 | Winnard | 604/236 |
| 3,831,629 | 8/1974 | Mackal | 137/525 |
| 3,901,246 | 8/1975 | Wallace | 251/342 |
| 4,143,853 | 3/1979 | Abramson | 251/149.1 |
| 4,310,140 | 1/1982 | Boomer et al. | 251/5 |
| 4,340,049 | 7/1982 | Munsch | 604/905 |

*Primary Examiner*—A. Michael Chambers

[57] ABSTRACT

The automatic check valve is proposed to be used with male luer fittings which are the standard on many medical applications. The valve body is a piece of resilient tubing into which a stopper having an oval sealing ring is placed. Inserting the round male luer fitting causes the tube to be made round releasing the seal of the stopper at two points on the minor axis of the oval shape.

7 Claims, 4 Drawing Figures

CATHETER CHECK VALVE

FIELD

Surgery, Cannula

This invention relates to a fluid check valve of simplified construction being one piece to be used with systems common in medical applications. The one piece is a stopper having an oval sector which is interference fitted into a tube and a smaller end. The other elements used are parts expected to be common in the field such as tapered luer fitting and tubing sized for connection to luer fittings. Luer fittings are the standardized (American National Standard Z-70.1) fittings used on hypodermic syringes, intravenous catheters and many medical devices.

The valve would work very well with liquid or gases and is particularly suited to medical applications but is not limited to those applications. Other configurations of similar proportions but differing sizes would equally well. Combinations with other elements such as extension rods or various housings are also possible.

A prior valve now in common use has a rigid housing to accept a tapered fitting and an elastomeric element within the housing that compresses axially to provide the valve action. This valve is normally installed in a tube when in use. The present valve eliminates the housing and offers a simplier approach to both sealing and assembly. Other valves have more than two elements such as using a spring or a two part seat. While these valves work well, they are more expensive to manufacture.

Having fewer elements also reduces field problems with fluid compatibility or storage life. The materials used can be chosen to suit the use with many combinations of tubing material and stopper materials being workable. Tubing could be plastic or rubber with or without reinforcement in a variety of thicknesses. The stopper would preferably be plastic because the shape is easily molded but metal or any hard material could be used.

The design of plugs and stoppers for various resilient tubes or bores is well developed. It is well known that a barb can be provided which will limit movement by digging into the wall of the mating part or increasing the stress at a narrow line. Barbs also improve sealing when used to make the fit tighter. A resilient tube is much less likely to relax to a larger size or stress crack if a narrow width barb is used rather than increasing the size of the entire fitting.

The valve of the invention offers the simplicity and proven design of a barbed stopper. It is very simple to make and install. It has no moving parts other than its tubing which expands and contracts. The part is as durable as the rest of the assembly since it is a small addition to an existing system. The use of a resilient tube allows good sealing to the syringe or other pressurizing system.

The above and further objects and novel features of the invention will be more apparent from the following description and accompanying drawings. The drawings are for illustration and should not be taken to limit the scope of the invention.

In the drawings like reference numerals refer to like parts in the several views.

Figure 1:
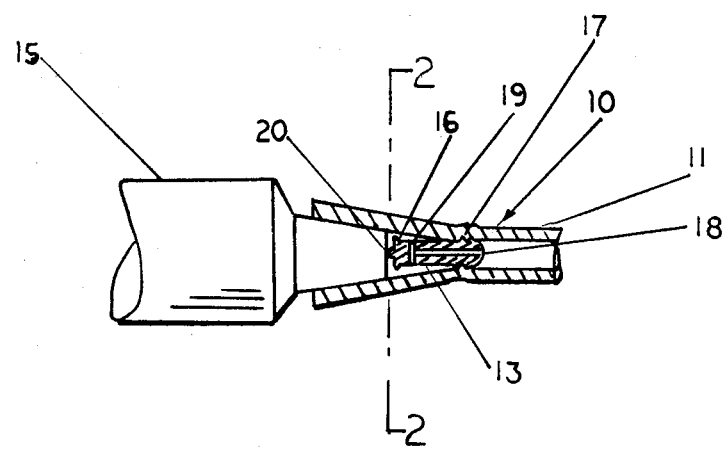
FIG. 1 is a view in axial cross section through the assembled valve showing the smaller aspect of the oval vertical. The tapered nozzle of an inflation syringe is shown inserted.
Figure 2:
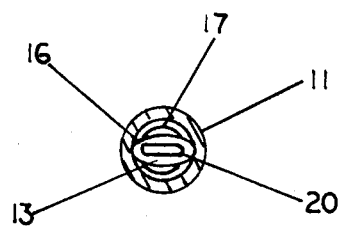
FIG. 2 is a view in cross section through the assembled valve being taken along the line 2—2 of FIG. 1.

As will be apparent from the above, three embodiments of the valve in accordance with the invention are shown. The first embodiment is shown in FIGS. 1 and 2, the second in FIG. 3 and the third in FIG. 4. Although the illustrations of the valve are particularly suited as check valves in a catheter to be used with a luer taper syringe, it is to be understood that the valve is useful in a number of other applications as will become apparent from the following description.

In FIG. 1 is shown a valve assembly generally designated by the reference character 10 in which a tube 11 is shown with a plug 13 inserted and a syringe 15 also inserted. Plug 13 is of a particular shape and size to effect a tight seal of tube 11 when the syringe 15 is not inserted. This is accomplished by a barb or raised portion 16 at one end of plug 13. Plug 13 and barb 16 are oval or the shape of a flattened circle at the end with barb 16. The size of barb 16 is set to be an interference fit to tube 11 causing the barb to sink into tube 11 slightly or at least to cause a small distortion in the resilient tube 11. Immediately after the barb 16 the body of plug 13 becomes considerably smaller and might have a clearance to tube 11. At the end opposite barb 16 there is one or more raised portions or barbs 17 that are also an interference fit to tube 11. Between barb 16 and barb 17 is shown a crosshole 19 connecting with an axial hole 18. Tube 11 need not be any particular length as long as it is long enough to contain the plug and the tip of an activating means such as syringe 15.

FIG. 2 shows plug 13 viewed from the end with barb 16. The section being taken through tube 11 between barb 16 and the end of syringe 15. Tube 11 is shown as it would be shaped by having syringe 15 in place. Without syringe 15, tube 11 would conform to the shape of barb 16. A raised portion 20 is shown that could be included on plug 13. Barb 17 is interference fitted to the tube 11.

Figure 3:
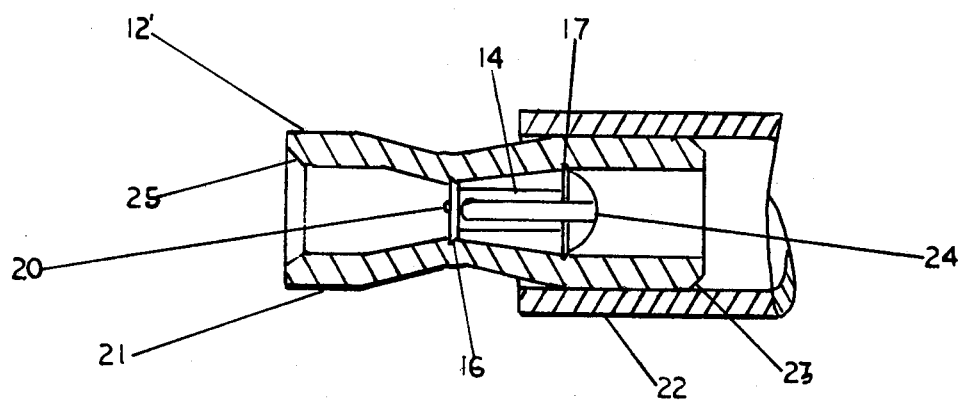
FIG. 3 is a view in axial cross section through the outer tube of an alternative embodiment of an assembled valve and partially sectioned plug shown inserted into a mating part.

In FIG. 3. a second alternative embodiment of the valve of FIG. 1 is shown generally as 12' having an outer tube 21 that is made with a wall thickness to suit adapting it to some standard part such as housing 22. Tube 21 has a tapered end 23 and a lead 25 both sized and shaped to suitable adaptive means. Plug 14' is a alternative embodiment of plug 13 of FIG. 1. Plug 14' has a slot 24 that may be only on one side or on both sides and having a slight depth. Slot 24 breaks barb 17 making barb 17 non-continuous.

Figure 4:
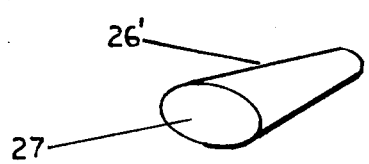
FIG. 4 is a perspective side elevation of a third alternative embodiment of the plug alone.

In FIG. 4 is shown the simplest embodiment of plug 26' being a form tapered axially in the manner a stopper or cork might be and having an oval cross section along its entire length. The plug 26' would be sized so the larger end would be a tight fit to the resilient tube it was meant to be mated with. The angle of the taper would be suited to make insertion easy and to allow the plug 26' to lock in place as a properly shaped cork fits a bottle. The features of plug 13 or plug 14 such as barb 16, barb 17, slot 24 or raised section 20 could all or any one be included in plug 26'. In addition the face 27 of the larger end of plug 26' is shown approximately at right angles to the axis of the body but it could be at a slight angle in any plane and could be rounded or concave as well.

As an example of the use of the invention, a catheter or tube 11 sized to engage the leading edge of a Luer tip syringe 15 and become interference fitted as the larger part of the Luer tip was pushed axially into the tube is selected. Other sizes of tubing and other tips could be used but the Luer fittings are very common and a good application of the device. The tubing 11 would be made of a resilient material such as PVC plastic or a rubber and syringe tips 15 are often glass, metal or hard plastic.

The plug 13 is to made of a relatively stiff material such as metal or plastic and is designed to fit into a particular size tube with enough interference to cause a leaktight seal. The smaller end with hole 18 has a slight lead to facilitate starting insertion into tube 11. Directly after the lead one or more barbs 17 may be placed that would be designed to help lock the plug 13 in axial position. The barbs 17 could take the form of a series of spikes or a discontinous ring as well as the more common continous ring since there is no need to effect a seal at that point. At barb 17 the plug 13 could be round or some other shape as long as there was reasonable contact with tube 11 to stabilize plug 13. The end of plug 13 having raised section or barb 16 is carefully shaped to produce a leaktight seal to tube 11 when syringe 15 is not in place. The shape is important because to effect a seal with a barbed fitting requires pressure from barb 16 to be exerted on tube 11 around the entire periphery of barb 16. The ovality of plug 13 forces a high contact pressure at the major axis and the shape at the major axis ends must be sufficiently tapered to ensure good contact at the minor axis. The height of the minor axis of barb 16 must be less than the diameter of the tip of a luer syringe 15 or other actuating means. The difference in the diameter of the tip of syringe 15 and the minor axis of barb 16 will determine the flow rate of the open valve, when passing air a small difference would suffice.

When the tip of syringe 15 is fully inserted into the tube 11, an effective seal with tube 11 will be formed due to the interference fit of the resilient tube 11. Full insertion would place the tip of syringe 15 next to plug 13. Plug 13 could actually be forced slightly deeper into tube 11 by insertion of the syringe 15 but as soon as the insertion force was removed the resiliency of tube 11 would cause the syringe 15 to back away from plug 13 slightly and leave a passage. To ensure a passage for thicker fluids a raised portions 20 could be added. Other means to accomplish the same effect might include crowning the end of plug 13 or angling it slightly. Many shapes for raised portion 20 could be used as long as they reduced the contact area with syringe tip 15.

Flow over barb 16 would possibly leak by barb 17 but to ensure a flow passage a crosshole 19 connecting to a partial axial hole 18 could be provided. In alternative embodiment 14' of FIG. 3 slot 24 is shown. FIG. 4 shows a plain tapered plug 26 that would depend on a size difference end to end and the amount of difference in the dimensions of the minor axis of end 27 of plug 26' and the diameter of the actuating tip or tube. The actuating tip 15 would lift the outer tubing 11 far enough from plug 26' to put the minor axis out of contact the entire length of plug 26'.

Removing syringe 15 partially would allow tube 11 to return to position tightly sealing plug 13. At the point sealing takes place, syringe 15 is still engaged in tube 11 tightly enough to effect a seal around itself thereby ensuring minimal leakage as the syringe 15 is withdrawn. Since tube 11 is expanded or distorted by syringe 15 only in the area of barb 16 the opposite end of plug 13 with barb 17 remains in tight contact with tube 11 at all times thereby stabilizing the position of plug 13.

Where tube 11 of FIG. 1 is a plain tube that might be one end of a much longer tube having other features or attachments the alternative embodiment of FIG. 3 shows a tube 12' that is sized to act as a housing to make a valve assembly to be inserted into another device. Tube 12' could be provided with a lead 25 to make insertion of an actuating tip or tube easier and also might have a lead 23 on its outer diameter to make itself easier to insert into another device. Since the wall of tube 12' would be heavier than needed to merely make the valve workable, other features such as grips or stops could be included. Tube 12' could be either an extruded tube with secondary modifications or it could be a molded part. Tube 12' could be fitted into fitting 22 and be fixed by suitable means such as gluing. If fitting 22 is not flexible the active area of tube 12' over barb 16 must remain outside of fitting 22 or a recess provided to allow distortion of tube 12'.

I claim:

1. A check valve to govern fluid flow in tubing said tubing being resilient and elastic enough to be distorted by an axially tapered plug said plug being essentially oval in cross section at least at one end and having dimensions such that the major axis distorts the tubing into which the plug is installed into a flattened shape with a minor axis dimension considerable smaller than the tubing diameter so that a rigid tube or other device of slightly larger outer diameter than the tubings inner diameter when inserted into said resilient tube causes the resilient tubing to take the shape and size of the rigid tube at the minor axis of the plug thereby partially separating the resilient tubing from sealing contact with the tapered plug forming a passage for fluid flow past the tapered plug until the rigid tube is removed and the resilient tubing again returns to tight contact with the tapered plug thereby closing the flow passage.

2. A check valve as in claim 1 having a tapered plug with a raised portion or barb at the larger end to ensure tubing contact in a narrow band all or partially around the circumference of the plug.

3. A check valve as in claim 1 having a plug with one end oval and large enough to interference fit into a straight bore tube and the other end smaller and of either oval or some other shape said smaller end having a means of air passage such as a slot or slots on the surface or a partial axial hole meeting a crosshole said means of air passage extending to near the larger end but not past it.

4. A check valve as in claim 1 where the outer tubing is sized and formed into a shape that is adaptive to assembly with other devices by having rounded ends, stops or special shapes on its outer surface.

5. A check valve as in claim 1 having an oval tapered plug that has a retention means on its smaller end in the form of a circumferential raised sector or barb or a series of protrusions designed to force into the outer tubing or a surface suitable to be bonded or joined to the tube.

6. A check valve as in claim 1 where the tapered plug has a means at its larger oval end to reduce the flat surface area by adding a protrusion or crowning or causing the face of the plug to be in an angular plane with respect to the plug axis.

7. A check valve as in claim 1 where the plug has a shape other than round and where one axis is smaller than the diameter of the tube it is intended to seal.

* * * * *